United States Patent
Lach

(10) Patent No.: US 9,453,693 B2
(45) Date of Patent: Sep. 27, 2016

(54) METHOD OF CONTROLLING THE SATURATION LEVEL OF A GENERATED GASEOUS STATE FLUID

(75) Inventor: Raymond Lach, Montreal (CA)

(73) Assignee: MAXI-THERME INC., Montreal, Quebec (CA)

( * ) Notice: Subject to any disclaimer, the term of this patent is extended or adjusted under 35 U.S.C. 154(b) by 1051 days.

(21) Appl. No.: 13/545,441

(22) Filed: Jul. 10, 2012

(65) Prior Publication Data

US 2014/0014311 A1    Jan. 16, 2014

(51) Int. Cl.

| | |
|---|---|
| *F28F 27/00* | (2006.01) |
| *A61L 2/07* | (2006.01) |
| *G05D 22/02* | (2006.01) |
| *A61L 2/24* | (2006.01) |
| *F28B 3/06* | (2006.01) |

(52) U.S. Cl.
CPC .................. *F28F 27/00* (2013.01); *A61L 2/07* (2013.01); *A61L 2/24* (2013.01); *G05D 22/02* (2013.01); *A61L 2202/24* (2013.01); *F28B 3/06* (2013.01)

(58) Field of Classification Search
CPC ........... A61L 2/07; F28F 27/00; G05D 22/02
USPC ......... 165/200, 285, 286, 294, 296; 237/2 R, 237/9 R; 422/26
See application file for complete search history.

(56) References Cited

U.S. PATENT DOCUMENTS

| | | | |
|---|---|---|---|
| 3,845,627 A * | 11/1974 | Hutchinson .................. | 60/641.3 |
| 4,149,403 A | 4/1979 | Muldary et al. | |
| 6,116,259 A * | 9/2000 | Stoy et al. ......................... | 137/9 |
| 2002/0085945 A1* | 7/2002 | Florkey et al. .................... | 422/3 |
| 2007/0144457 A1* | 6/2007 | Russoniello et al. ...... | 122/448.3 |
| 2007/0274858 A1* | 11/2007 | Childers et al. ................ | 422/28 |
| 2011/0000281 A1* | 1/2011 | Deacon .................. | G01N 25/60 |
| | | | 73/25.04 |
| 2011/0000287 A1* | 1/2011 | Bacic .......................... | 73/112.01 |

OTHER PUBLICATIONS

Young, Jack. "Steam Sterilization: Scientific Principles." Sterilization Technology for the Health Care Facility. 2nd Edition. Gaithersburg, Maryland: Aspen Publication, 1997. 124-133.

* cited by examiner

*Primary Examiner* — Travis Ruby
(74) *Attorney, Agent, or Firm* — Fraser Clemens Martin & Miller LLC; James D. Miller

(57) ABSTRACT

The method of controlling the saturation level of a gaseous state fluid generated at an outlet of a gaseous state fluid generation system comprises measuring a reference parameter of the fluid other than the saturation level itself, with the reference parameter being representative of the saturation level, and selectively superheating the fluid as a response to the measured reference parameter until the reference parameter falls within an acceptable range of reference parameter values.

18 Claims, 1 Drawing Sheet

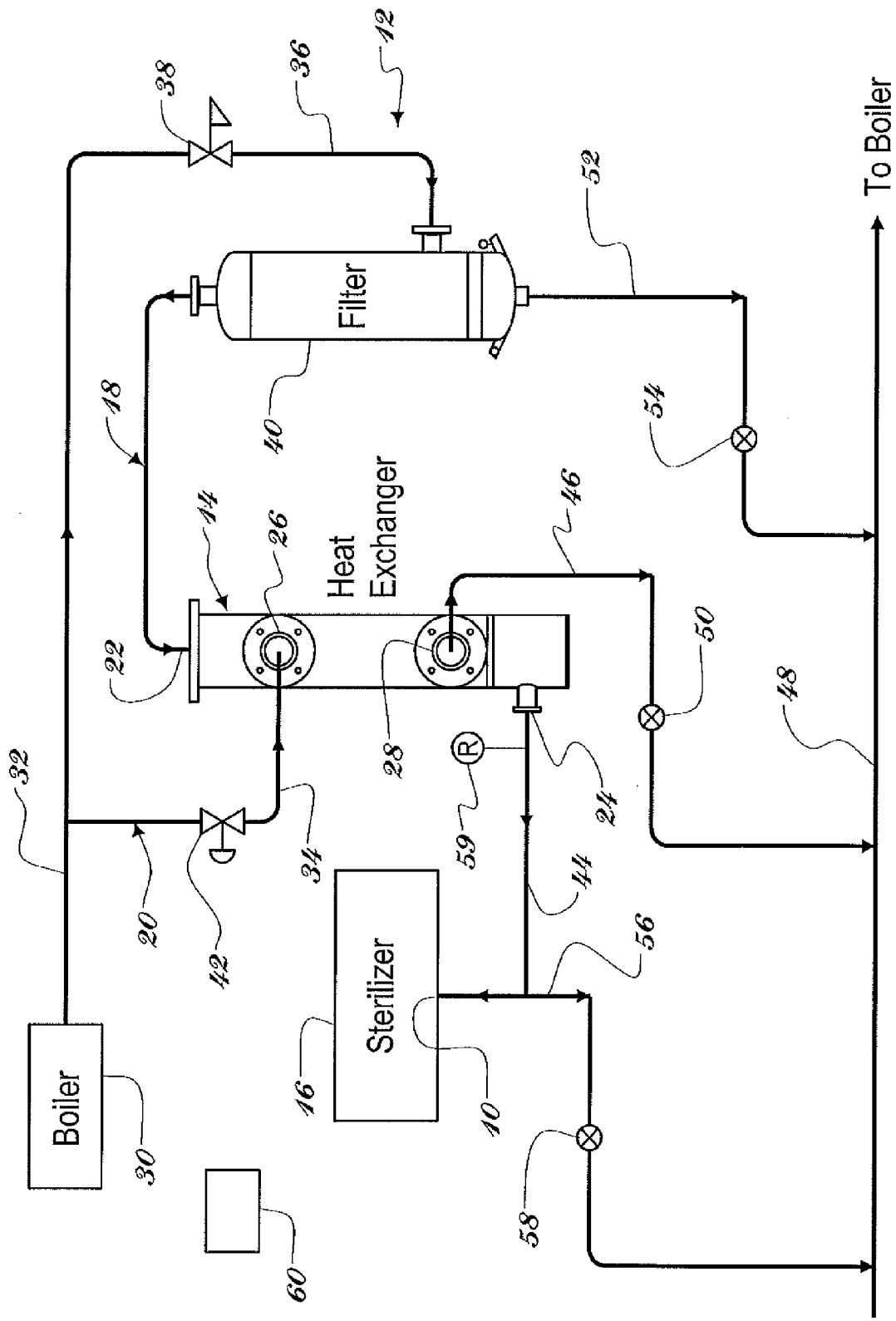

METHOD OF CONTROLLING THE SATURATION LEVEL OF A GENERATED GASEOUS STATE FLUID

FIELD OF THE INVENTION

The present invention relates to a method of controlling the saturation level of a gaseous state fluid, such as steam, that is generated by a gaseous state fluid generation system.

BACKGROUND OF THE INVENTION

Surgical tool sterilizers use hot steam to sterilize surgical tools to decrease the likelihood of infections. The sterilizers comprise a housing wherein steam is injected after the tools have been inserted therein.

One problem with sterilizers is that use of steam will often result in water droplets appearing on the surgical tools. This is problematic as it may result in infections on patients operated with said tools and sometimes requires tools to be repeatedly sterilized before they are in an acceptable condition. In some cases where tools could not be sterilized properly, the operations on the patients even have to be cancelled entirely. One way to circumvent this problem is to provide steam in the sterilizers having a higher saturation level, or in other words wherein the steam quality or "dryness" will be higher. Sterilizers usually require to be provided with steam having a saturation level, also called the steam quality, of 97% or more, meaning that the liquid-state water micro-droplets carried by the steam will be 3% or less. This is likely to reduce risk of infections resulting from condensed water droplet formation on the surgical tools that originate from the injected steam. Control of steam saturation is normally accomplished at the boiler itself.

The challenge in controlling the saturation level of steam is twofold.

Firstly, the steam generated at the boiler for the sterilizer is conveyed through the large hospital building piping system. This allows the steam to loose energy during circulation through the pipes. So although the boiler may in fact generate steam with an appropriate quality, the steam that is outputted in the sterilizer might not be of adequate quality. Furthermore, the ambient parameters in the hospital might change over time, which can influence the steam quality. For example, the steam demand usually greatly varies at the hospital which requires the boiler to work at widely varying debit rates, resulting in varying steam quality over the entire hospital steam system including at the inlet of the sterilizer. Also, air or other non-condensable gases that will change the steam parameters and steam quality may be found in varying proportions from one hospital to the other within the steam pipes. So even if at one time the steam quality at the sterilizer is adequate, at another time the steam quality at the sterilizer might be inadequate for a same boiler due to circumstances identified above, among others.

Secondly, it is complex to measure the actual saturation level of steam. The present inventor is not aware of an efficient method of automatically measuring the saturation level at regular time intervals or, better yet, continuously. Manipulations need to be accomplished on the premises by an operator to first sample steam and then measure the saturation level in the sampled steam for example with a calorimeter, which is tedious and time-consuming. This is not an acceptable solution when steam saturation needs to be measured and controlled on a continuous basis since it would require a proficient operator to remain near the sterilizers for that purpose alone.

SUMMARY OF THE INVENTION

The present invention relates to a method of controlling the saturation level of a gaseous state first fluid generated at an outlet of a gaseous state fluid generation system, the gaseous state fluid generation system comprising a first fluid line circulating the first fluid therein, a second fluid line circulating a second fluid therein and a heat exchanger wherein the first fluid is heated by the second fluid so as to have the first fluid be in gaseous state at least at a first fluid outlet of the heat exchanger which is distinct and in fluid communication with the outlet of the gaseous state fluid generation system, said method comprising:

a) generating gaseous state first fluid at the outlet of the gaseous state first fluid generation system and calibrating the gaseous state fluid generation system by:
  i) controlling a heat exchange value between the first and second fluids within the heat exchanger to obtain a set value for a reference parameter measured at a reference position on said first fluid line, with the reference parameter being representative of the saturation level of the first fluid;
  ii) determining a saturation level of the gaseous state first fluid at the outlet of the gaseous state fluid generation system;
  iii) if the saturation level of the gaseous state first fluid determined at step (ii) does not correspond to a first target saturation level of the gaseous state first fluid, controlling the heat exchange value of the heat exchanger to iteratively obtain different reference parameter values measured at the reference position and repeating step (ii) for each iteration of the reference parameter values until the first target saturation level of the gaseous state first fluid is determined at step (ii), with the first target saturation level of the gaseous state first fluid used to define an acceptable range of saturation levels; and
  iv) identifying the reference parameter value measured when the target saturation level is determined as the first target reference parameter value, with the first target reference parameter value used to define an acceptable range of reference parameter values;

and once the gaseous state fluid generation system is calibrated per step (a):

b) measuring the reference parameter at the reference position while gaseous state first fluid is generated at the outlet of the gaseous state first fluid generation device;

c) comparing the value of the reference parameter measured in step (b) to the acceptable range of target reference parameter values; and d) if the value of the reference parameter measured in step (b) falls outside of the acceptable range of reference parameter values, modifying the heat exchange value of the heat exchanger and repeating steps (b) and (e) until the value of the reference parameter measured in step (b) falls within the acceptable range of the reference parameter values, consequently controlling the saturation level of the gaseous state first fluid to have it fall within the acceptable range of saturation levels at the outlet of the gaseous state fluid generation system.

In one embodiment, the reference parameter comprises a reference temperature, the reference position is located between the outlet of the heat exchanger and the outlet of the gaseous state fluid generation system, the target reference parameter value comprises a target temperature value and the first fluid is in superheated state at least at the reference position when the first fluid saturation level is at its first target saturation level at the outlet of the gaseous state fluid generation system.

In one embodiment, the reference position is located near the outlet of the heat exchanger.

In one embodiment, controlling and modifying the heat exchange value comprises controlling and modifying one of the second fluid debit through the heat exchanger, the temperature of the second fluid that flows through the heat exchanger, the second fluid pressure through the heat exchanger and a combination thereof.

In one embodiment, the acceptable range of reference parameter values comprises reference temperature values equal to or above the target reference temperature value.

In one embodiment, step (a)(iii) further comprises, if the saturation level of the first fluid determined at step (ii) does not correspond to a second target saturation level of the first fluid, the step of further controlling the heat exchange value of the heat exchanger to iteratively obtain different reference parameter values measured at the reference position and repeating step (ii) for each iteration of the reference parameter values until the second target saturation level of the first fluid is determined at step (ii), with the acceptable range of saturation levels of the first fluid being defined between the first and second target saturation levels of the first fluid; and wherein step (a)(iv) further comprises the step of identifying the reference parameter value measured when the second target saturation level is determined as a second target reference parameter value, with the acceptable range of reference parameter values being defined between the first and second target reference parameter values.

In one embodiment, the step (a)(ii) comprises sampling gaseous state first fluid at the outlet of the gaseous state fluid generation system and determining the gaseous state first fluid saturation level from the sampled gaseous state first fluid.

In one embodiment, in step (a)(ii), determining the saturation level of the sampled gaseous state first fluid comprises measuring a sampled steam parameter other than the saturation level and correlating a saturation level with this sampled steam parameter.

In one embodiment, the gaseous state fluid generation system further comprises an electronic circuit capable of storing data therein, capable of processing data, and capable of data input and output, the step (a)(iv) comprises inputting and storing as data the acceptable range of reference parameter values in the electronic circuit, the step (b) comprises inputting as data the reference parameter value read in step (b), the step (c) comprises comparing through use of the electronic circuit the inputted reference parameter value read in step (b) to the stored acceptable range of reference parameter values and the step of modifying the heat exchange value of the heat exchanger in step (d) comprises automatically modifying through control by the electronic circuit the heat exchange value of the heat exchanger.

In one embodiment, the gaseous state fluid generation system further comprises an electronic circuit capable of storing data therein, capable of processing data, and capable of data input and output, the step (a)(iv) comprises inputting and storing as data the acceptable range of reference parameter values in the electronic circuit, the step (b) comprises inputting as data the reference parameter value read in step (b), the step (c) comprises comparing through use of the electronic circuit the inputted reference parameter value read in step (b) to the stored acceptable range of reference parameter values and the step of modifying the heat exchange value of the heat exchanger in step (d) comprises automatically modifying through control by the electronic circuit the heat exchange value of the heat exchanger.

In one embodiment, the step of calibrating the gaseous state first fluid generation system in step (a) comprises repeating steps (i) to (iv) at different first fluid line pressure values to obtain an acceptable range of reference parameter values for each first fluid line pressure value; and step (c) comprises comparing the reference parameter value measured in step (b) to the acceptable range of reference parameter values for a corresponding first fluid line pressure value that corresponds to an effective first fluid line pressure value.

In one embodiment, the effective first fluid line pressure value is measured on the first fluid line when the reference parameter value is measured in step (b).

In one embodiment, the reference parameter value measured in step (b) is compared in step (c) to a modified range of acceptable reference parameter values which is calculated based on the acceptable range of reference parameter values and on an effective first fluid line pressure value.

In one embodiment, the effective first fluid line pressure value is measured on the first fluid line when the reference parameter value is measured in step (b).

In one embodiment, the step (b) comprises one of continuously measuring the reference parameter value, discretely measuring the reference parameter value at regular or irregular time intervals and punctually measuring the reference parameter value.

In one embodiment, the heat generation system further comprises a coalescing filter on the first fluid line upstream of said heat exchanger.

In one embodiment, the first fluid is steam.

In one embodiment, said gaseous state first fluid generation system further comprises a sterilizer connected to the outlet of the steam generation system for injecting steam generated by the gaseous state first fluid generation system in said sterilizer.

The present invention also relates to a method of controlling the saturation level of a gaseous state fluid generated at an outlet of a gaseous state fluid generation system, comprising: measuring a reference parameter of the fluid other than the saturation level itself, with the reference parameter being representative of the saturation level, and selectively superheating the fluid as a response to the measured reference parameter until the reference parameter falls within an acceptable range of reference parameter values.

In one embodiment, said reference parameter is a temperature of the gaseous state fluid and the acceptable range of reference parameter values is an acceptable range of temperature values.

DESCRIPTION OF THE DRAWINGS

The annexed single drawing figure is a schematic view of a gaseous state fluid generation system for controlling the saturation level of a gaseous state fluid according to the present invention.

DETAILED DESCRIPTION OF THE EMBODIMENTS

The present invention relates to a method of controlling the saturation level of a gaseous state first fluid generated at an outlet 10 of a gaseous state fluid generation system 12 shown in the single annexed figure of drawings. To control the saturation level of the gaseous state first fluid, the first fluid is selectively variably heated, such as by circulating the first fluid and a second hotter fluid through a heat exchanger 14, as detailed hereinafter.

Although it is not limited to such use, the present invention is particularly adapted for use with a sterilizer 16 wherein the gaseous state first fluid will be used to sterilize tools such as surgical tools. Use of steam as the gaseous state first fluid is commonplace in a sterilizer, and generally water (including in its steam state) can consequently be used as the first fluid. The second fluid may be any suitable fluid for heating the first fluid, and the second fluid may also be water in its steam state if appropriate temperatures/pressures are used, as detailed hereinafter.

In the embodiment depicted in the annexed drawing figure, the gaseous state first fluid generation system 12, which may also be called the steam generation system 12 if the first fluid is steam, comprises a first fluid line 18 circulating medium-pressure steam therein, a second fluid line 20 circulating high pressure steam therein and heat exchanger 14 wherein the medium pressure steam in the first fluid line 18 is superheated by the high pressure steam in the second fluid line 20. The fact that the steam pressure is higher in the second fluid line 20 than in the first fluid line 18 allows the steam temperature to be greater in the second fluid line, allowing heat transfer to occur from the second fluid to the first fluid. This heat transfer will in fact superheat the steam in the first fluid line, thereby increasing the steam saturation level or, in other words, increasing the steam dryness and quality.

As known in the art, the first and second fluid lines are in thermally conductive proximity within heat exchanger 14, but the first and second fluids are not allowed to mix. Preferably, the high pressure steam will be allowed to condense in the second fluid line within heat exchanger 14, since condensation is highly exothermic and consequently thermodynamically efficient.

Heat exchanger 14 has a first fluid line inlet 22 where the medium pressure steam enters the heat exchanger 14, a first fluid line outlet 24 where superheated steam exits the heat exchanger 14, a second fluid line inlet 26 where the high pressure steam enters the heat exchanger 14, and a second fluid line outlet 28 where the condensate (resulting from the condensed high-pressure steam) exits the heat exchanger 14. It is noted that the first fluid outlet is schematically illustrated on the drawing figure at an actual outlet coupling 24 of heat exchanger 14, it could also be located at the actual downstream end of tubes (not shown) through which the first fluid flows within heat exchanger 14.

Steam generation system 12 also comprises a boiler 30 that creates steam from water fed into boiler 30 from a suitable liquid-state water source (not shown) that may include the municipal water tap combined with return water from steam generation system 12 itself. The steam created at boiler 30 is conveyed into a main high pressure steam line 32 that branches into a secondary high pressure line 34 to feed high pressure steam into heat exchanger 14; and into a secondary medium pressure line 36 located beyond a pressure reduction valve 38 for feeding medium pressure steam into heat exchanger 14. A pressure sensor (not shown) may be installed downstream of valve 38.

A coalescing filter 40 is installed on medium-pressure line 36 to remove water droplets carried by the steam. Coalescing filter 40 is optional and should not significantly influence the pressure in medium pressure line 36 downstream of filter 40, compared to the pressure upstream of filter 40.

A control valve 42 controls the debit of high pressure steam into heat exchanger 14.

Superheated steam exiting from the heat exchanger first fluid line outlet 24 is conveyed through a superheated steam line 44 to the outlet 10 of steam generating system 12 for being fed into sterilizer 16. Superheated steam line 44 may—and usually will—be long depending on the distance that separates the heat exchanger 14 from the sterilizer 16. Usually the heat exchanger is installed in the boiler room of the hospital, while the sterilizer is located near the surgical operation rooms. Steam energy loss is likely to occur along superheated steam line 44.

A condensate outlet line 46 recuperates condensate in the second fluid line that exits the heat exchanger through the heat exchanger second fluid line outlet 28. Condensate line 46 is connected to a water return line 48 that conveys liquid-state water to a suitable destination, for example back to boiler 30. A liquid purge valve 50 is installed on condensate line 46 to ensure that only liquid-state water circulates through water return line 48.

A filter water line 52 equipped with its own liquid purge valve 54 connects filter 40 to water return line 48 to evacuate water recuperated in filter 40, while the medium-pressure gaseous state steam circulated through filter 40 will be conveyed to heat exchanger 14.

A liquid state water purge line 56 equipped with its own liquid purge valve 58 branches off the superheated steam line 44. The liquid purge valve 58 is set so that liquid-state water purge line 56 would be minimally used while steam demand exists in sterilizer 16. However, particularly if steam stagnates in line 44 when there is no steam demand at sterilizer 16, the steam may condense in superheated steam line 44, requiring that this liquid water be purged from superheated steam line 44, which is allowed by liquid purge valve 58. Liquid-state water purge line 56 connects to water return line 48 downstream of steam purge valve 58.

The first fluid line 18 defines an upstream end at pressure reduction valve 38 and a downstream end at the outlet 10 of the steam generation system 12; while the second fluid line 20 has an upstream end that can be located either at control valve 42 or literally at boiler 30 and a downstream end that can be located at steam purge valve 50 or at any suitable position downstream of second fluid line outlet 28, including at boiler 30 if water return line 48 is linked thereto. It is noted that although steam has been described as being fed through the first fluid line inlet 22 of the heat exchanger, liquid-state water (from another source than boiler 30) could conceivably be fed through first fluid line inlet 22. Steam (or more generally, gaseous state first fluid) will of course be generated at the outlet 24 of heat exchanger 14 in any event. Also, although steam has been described as being fed into the heat exchanger 14 through the second fluid line inlet 26 and condensate has been described as exiting the second fluid line outlet 28, any suitable second fluid in liquid or gaseous state could be fed into the heat exchanger as long as heat transfer from the second fluid to the first fluid occurs. For example, the second fluid could both enter and exit heat exchanger 14 in liquid state, could both enter and exit heat exchanger 14 is gaseous state, or could enter in gaseous state and exit in liquid state.

The connection between the first fluid line outlet 24 of the heat exchanger 14 and the outlet 10 of the steam generation system 12 through superheated steam line 44 allows the steam that flows out of the first fluid line outlet 24 of the heat exchanger 14 to be conveyed to and flow out of the outlet 10 of the steam generation system 12 for use in the sterilizer. However, since these outlets 24, 10 are distally located, energy losses occur, resulting in some measure of saturation level reduction of the steam being provided to sterilizer 16. This means that steam quality would be affected if nothing is done about it, with the undesirable consequence that water micro-droplets could form on the surgical tools, thereby rendering the sterilization procedure less efficient and possibly unacceptable. One way of avoiding this problem is to control the saturation level in the steam generated at the outlet 10 of the steam generation system 12 to provide dryer steam as per the present invention's teachings. More particularly, the saturation level of the steam generated at the outlet 10 of the steam generation system 12 will be controlled to be within a range of acceptable values, taking into account the steam energy loss along high pressure steam line 32, medium pressure steam line 36 and superheated steam line 44, together with variations of the steam quality provided by boiler 30. This control of the steam saturation level is clone by controlling the heat exchange value within the heat exchanger to heat, and more specifically to superheat, the first fluid line steam within heat exchanger 14.

According to the present invention, the method of controlling the saturation level of the gaseous state first fluid at the outlet 10 of the gaseous state fluid generation system 12 comprises generating steam at the outlet 10 of the steam generation system 12 and using this steam generation to calibrate the steam generation system 12. The calibration is to be accomplished at least initially, and may be accomplished afterwards punctually as required. The calibration comprises first controlling a heat exchange value between the steam and the second fluid within the heat exchanger to obtain a set value for a reference parameter measured at a reference position on the first fluid line. This representativeness means that if the reference parameter is modified, the saturation level will also be modified, proportionately or not, in a predictable way. One example of a reference parameter is the temperature of the first fluid, and one example of a reference position is that shown at 59 in the annexed figure of drawings, namely at the outlet of the heat exchanger 14. The control of the heat exchange value between the first and second fluids in the heat exchanger 14, comprises controlling one of:

the second fluid debit through the heat exchanger 14 by adjusting control valve 42;

the second fluid temperature at the second fluid line inlet 26 of the heat exchanger 14 for controlling the temperature of the second fluid flowing therein, for example by providing hotter steam from boiler 30;

the second fluid pressure through the heat exchanger 14; and a combination of one or more of controlling the second fluid debit, temperature and pressure;

to obtain the desired fixed reference parameter value at the reference position. The heat exchange value may be variable in the heat exchanger 14 to obtain the set or fixed reference parameter value, for example if varying steam quality enters the heat exchanger. For example, control valve 42 may allow a variable flow rate of hot, high pressure steam to enter heat exchanger 14 to obtain a fixed reference parameter value at the reference position.

Parameters of the first fluid could also conceivably be controlled instead of controlling the second fluid parameters mentioned above, with the end result also being that the heat exchange value within heat exchanger 14 would be modified, although this is less of an attractive option since it is usually simpler to modify the above-noted parameters of the second fluid. Other parameters of the heat exchanger 14 or of any other element of the steam generation system 12 could also be modified, to selectively control the heat exchange between the first and second fluids.

The calibration of the steam generation system 12 then comprises determining a saturation level of the steam at the outlet 10 of the steam generation system 12. The determination of the steam saturation level can comprise sampling steam at the outlet 10 of the steam generation system 12, for example within the sterilizer 16, once the heat exchange value is set at the heat exchanger 14. In one embodiment, this step comprises recuperating a steam sample through a punctual manipulation by an operator and measuring the steam saturation level in this sample. This is done in any manner known in the art, for example by using a calorimeter. Suitable calorimeters can be such as those sold by Croll Reynolds Company Inc. located in Parsippany, N.J., USA; or by Keith Shuttleworth & Associates Ltd. located in Luton, United Kingdom. Determining the steam saturation level within the steam sample can include measuring a steam parameter other than the saturation level itself, such as pressure, and correlating a saturation level with this steam parameter.

If the determined steam saturation level does not correspond to a first target steam saturation level, the calibration of the steam generation system then comprises controlling the heat exchange value of the heat exchanger to iteratively obtain different parameter values measured at the reference position and repeating the step of determining the saturation level of the steam at the outlet of the steam generation system, for each iteration of the reference parameter values, until the first target steam saturation level is determined. The first target steam saturation level can be, for example and as noted above, 97%.

The first target steam saturation level is used to define an acceptable range of steam saturation levels. For example, the acceptable range of steam saturation levels could be any saturation level above 97%.

In one embodiment, the acceptable range of steam saturation levels can be defined with first and second target steam saturation levels that correspond to an upper and a lower limit. For example, the acceptable range of steam saturation levels could be any saturation level between a first target saturation level of 97% and a second target saturation level of 100%. In such a case, the initial calibration of the steam generation system comprises, if the determined steam saturation level does not correspond to a second target steam saturation level, the step of further controlling the heat exchange value of the heat exchanger to iteratively obtain different reference parameter values measured at the reference position and repeating the step of determining the saturation level of the sampled steam for each iteration of the reference parameter values until the second target steam saturation level is determined. As suggested above, controlling or modifying the heat exchange value comprises controlling or modifying one of the second fluid debit through the heat exchanger 14, the second fluid temperature at the heat exchanger second fluid line inlet 26, the second fluid pressure through the heat exchanger 14 and a combination thereof; or any other parameter of the second fluid, the first fluid, or the heat generation system, that would influence the heat exchange value between the first and second fluids.

The calibration further comprises identifying the reference parameter value measured when the first target saturation level is determined as a first target reference parameter value; and defining an acceptable range of reference parameter values on the basis of the first target reference parameter value.

If a second target saturation level has been measured, the calibration also comprises identifying the reference parameter value measured when the second target saturation level is determined as a second target reference parameter value. In such a case, the acceptable range of reference parameter values is defined between the first and second target reference parameter values instead on of the sole basis of the first target reference parameter value.

In one embodiment, as suggested above, the reference parameter value comprises a steam reference temperature value that will be measured at a reference position along the superheated steam line 44 anywhere between the first fluid line outlet 24 of the heat exchanger 14 and the outlet 10 of the steam generation system 12, preferably near the outlet 24 of the heat exchanger 14. In such a case, the first and second target reference parameter values comprise first and second target temperature value; and the acceptable range of the reference parameter value comprises any reference temperature value equal to or above the target reference temperature value if a single target temperature value is used, or any temperature falling between first and second target temperature values if two target temperature values are used. At least in the case where the temperature is the reference parameter being measured, the steam (first fluid) will have to be heated beyond its saturation point, i.e. the steam (first fluid) will be in superheated state, at least at the reference position, when the steam saturation level is at its target saturation level at the outlet of the steam generation system. Indeed, should the steam be below its saturation point at the reference position, modifications in heat exchange value may not result in modifications of the reference temperature where it is measured.

After the steam generation system is calibrated, the steam generation system 12 may be used under normal conditions without requiring the presence of a proficient operator to determine steam saturation levels while still allowing control of the saturation level at the outlet 10 of the steam generation system 12. To control the steam saturation level under normal use of the system 12, the method comprises measuring the reference parameter at the reference position when steam is generated at the outlet of the steam generation system 12. This step can comprise continuously reading the reference parameter, discretely reading the reference parameter at regular or irregular time intervals or even punctually reading the reference parameter for example at the start of the steam generation demand within sterilizer 16, although the latter case of only punctually reading the reference parameter is not ideal because the reference parameter may vary during use of sterilizer 16 and consequently it is preferable to read the reference parameter continuously or at least repeatedly. The reading is accomplished with any suitable parameter reading device 59, such as a temperature sensor for reading temperature. Reading device 59 has been positioned at one of many possible reference positions on the annexed drawing figure, with the reference position depending notably on what reference parameter is being read. For example, if reading device is a temperature sensor, it is understood that reading device 59 could indeed be positioned at any suitable position along first fluid line 18 downstream of heat exchanger first fluid outlet 14, including at steam generation system outlet 10 or near (but upstream of) purge valve 58.

Once a reference parameter value is measured or read, the method comprises comparing the reference parameter value to the target reference parameter value. This can be accomplished by a computer, as detailed hereinafter.

Finally, if the value of the reference parameter being read falls outside of the acceptable range of reference parameter values, the method comprises modifying the heat exchange value of the heat exchanger and repeating the steps of measuring the reference parameter at the reference position and comparing the value of the reference parameter thus measured to the acceptable range of reference parameter values until the measured reference parameter value falls within the acceptable range of the reference parameter values at the outlet 10 of the gaseous state fluid generation system 12. The acceptable ranges of the saturation level and of the reference parameter value can be defined by the system operator.

An example will hereinafter be provided.

Hospitals usually require that the steam at a sterilizer be provided at a pressure between 50 and 80 psig because industry sterilizers are set to be supplied with steam within that pressure bracket. Consequently, pressure reduction valve 38 will reduce the high pressure steam, for example 125 psig, to a set medium pressure value, for example 50 psig. Normally, this pressure value will remain constant. Also, hospitals require a minimum steam saturation level at the sterilizer 16 to sterilize the surgical tools. This minimum saturation level is usually 97%. It is further noted that, as explained in steam literature, it is not considered desirable to have superheated steam for sterilising purposes since superheated steam is considered less efficient than steam having a saturation level of 100% or less. So in the present example the acceptable range of steam saturation levels can be defined to be either: (a) 97% or more, in which case only a first steam target saturation level of 97% is used to define the acceptable range of saturation levels; or (b) 97% to 100%, in which case a second steam target saturation level of 100% is also used to define the acceptable range of steam saturation levels. The system operator decides what the acceptable range of saturation levels is between those two.

In the present example, temperature is the reference parameter measured on the first fluid steam line and sensor 59 is a temperature sensor located at the outlet 24 of the heat exchanger 14. Considering that energy loss will occur in line 44 leading to sterilizer 16, the steam saturation level will decrease between heat exchanger outlet 24 and steam generation system outlet 10. So even if steam having a 100% saturation level were to be generated at the boiler 30, energy loss within the pipes leading to sterilizer 16 will, more often than not, yield steam having a saturation level below 97% at downstream positions in the first fluid steam line such as at sterilizer 16 if nothing is done about it. To avoid this problem, steam will need to be superheated to a saturation level above 100% at the outlet 24 of heat exchanger 14 if a steam saturation level above 97% is to be obtained within sterilizer 16 to compensate this energy loss.

To control the superheating of the first fluid steam at heat exchanger 14 to obtain steam quality within the acceptable range of saturation levels (above 97% or between 97% and 100%) at sterilizer 16, the temperature is measured at sensor 59 to guide the control of the heat exchange value in heat exchanger 44. More particularly, the calibration step allows a specific target temperature value at sensor 59 to be correlated to the target saturation level at sterilizer 16. Theoretically, at a pressure of 50 psig, steam at 100% or less saturation would have a temperature of 298° F. (notwithstanding air or non-condensable gases). According to the teachings of the present invention, the steam will be superheated until a saturation level of 97% is determined at sterilizer 16. When this first target saturation level is reached, the temperature will be measured at sensor 59: this first target temperature value could be for example 303° F. at the 50 psig pressure (instead of the 298° F. that non-superheated steam would have). This superheated steam will yield, once the loss of energy along line 44 is accounted for, a usable saturation level of 97% at sterilizer 16. If the acceptable range of saturation levels is defined to be 97% or more, the acceptable range of reference temperature values will be 303° F. or more. However, if the acceptable range of saturation levels is defined between 97% and 100%, a second target temperature value at sensor 59 needs to be measured during the calibration step when a 100% saturation level is determined at sterilizer 16. For example, this second target temperature value could be 310° F. Consequently, the acceptable range of temperature values would then be any temperature between 303° F. and 310° F. at sensor 59.

As long as the temperature being read at the reference position remains within the acceptable range of temperature values (e.g. above 303° F. or between 303° F. and 310° F.), the heat exchange value will not be modified; but if the temperature value being read increases or decreases out of the acceptable temperature range, the heat exchange value of the heat exchanger will be modified accordingly, either to increase the heat transfer to the first fluid if the temperature dropped too low, or to decrease the heat transfer to the first fluid if the temperature increased too much. As noted above, the steam has to be in superheated state at least at the reference position where the temperature is read when the steam saturation level is at its target saturation level at the outlet of the steam generation system, since below the saturation point (in non-superheated state), the steam will be at constant temperature for variable saturation levels (between 1% and 100%) at the sensor 59 position and consequently the saturation level could not be controlled as a consequence of the measured steam temperature, except to bring it back to a level above the saturation point into a superheated state.

It is envisioned that the pressure in the first fluid line 18 might vary, although normally this pressure is set at a constant value through control of pressure reduction valve 38. If the pressure is constant, a single calibration (including the iterative procedure described above) is necessary to determine a target temperature value at sensor 59. However, if the pressure in first fluid line 18 should vary, then either a distinct calibration should be accomplished for each pressure value at which the system will operate, or mathematical calculations could be done to calculate what the target temperature values should be, taking into account the pressure variations, and based on the initial calibration. For example, if after a first calibration it is determined that the steam should be superheated of 5° F. over its saturation temperature at the reference position to obtain the desired first target saturation level at sterilizer 16, and knowing the saturated steam temperature value for a given pressure value (obtained from steam tables), the target temperature value could be calculated to be 5° F. over the saturated steam temperature value at any given pressure value.

Such pressure variations in the first fluid line 18 as described above could occur voluntarily or even involuntarily if the pressure reduction valve 38 malfunctions. Barring steam being provided outside of an acceptable pressure bracket (such as outside of the 50-80 psig bracket), the system 12 could continue to function even if steam pressure varies in the first fluid line 18. The above-mentioned pressure sensor provided near and downstream of pressure reduction valve 38 (or at any other suitable position on first fluid line 18) could be used to measure the pressure in first fluid line 18 to allow the control of the heat exchange value at heat exchanger 14 to be accomplished not only as a result of the temperature read at sensor 59 but also as a result of the pressure read on the first fluid line pressure sensor.

In one embodiment, the gaseous state fluid generation system 12 further comprises an electronic circuit 60 capable of storing data therein, capable of processing data, and capable of data input and output. Electronic circuit 60 may be in the form of a computer that is linked (e.g. wirelessly) to the different elements of the gaseous state fluid generation system 12 including the reference parameter reading device 59, the control valve 42, and a sterilizer control valve (not shown) at sterilizer 16 to control the steam injection in sterilizer 16. Data may be inputted at computer 60 through a user interface. Computer 60 may also receive system parameter data input such as from suitable sensors installed on steam generation system 12 including temperature sensors, pressure sensors (such as the pressure sensor near pressure reduction valve 38 if there is one), debit sensors or controllers, and the like. Use of a computer 60 allows the target reference parameter values that define the acceptable range of temperature values to be stored therein as data, once the acceptable range of temperature values is determined during the initial calibration stage of the steam generation system 12. The comparison between each reference parameter value read during normal operation of the steam generation system to the stored acceptable range of reference parameter values can be accomplished automatically through use of the computer 60 which will compare each read reference parameter value to the acceptable range of reference parameter values to determine if it is within the acceptable range of target reference parameter values. The step of modifying the heat exchange value of the heat exchanger 14 can comprise automatically modifying through use of the computer 60 this heat exchange value by increasing or decreasing the heat exchange value as a result of the previously mentioned comparison between each reference parameter value read by the reference parameter reading device 59 and the acceptable range of reference parameter values.

According to the present invention, the initial calibration step of the method is consequently used to empirically tie a target reference parameter value (such as a target temperature value) of the first fluid to the target saturation level of the first fluid—with the reference parameter value being representative of the saturation level. The measurement of the saturation level requiring the intervention of an operator is thus obviated during normal use (i.e. after initial calibration) of the first fluid generation system 12 and the saturation level may still be controlled through controlling the heat exchange value of the heat exchanger as a result of the reading of the reference parameter value. The latter can be chosen among parameters that may easily be automatically measured and read, such as the temperature of the first fluid.

If first fluid temperature is being read as the reference parameter, one advantage of the present invention is that it allows the steam to be superheated at the heat exchanger 14, although the resulting steam being injected in the sterilizer will in fact not be superheated: its saturation level might be in the 97%-100% range for example. It would be undesirable to have superheated steam injected in the sterilizer since it is known that superheated steam is not as efficient for use in sterilizing. However, since hospitals require a minimum saturation level such as 97% or more, the saturation level cannot be allowed to drop below that point. So by allowing the continuous adjustment of the steam saturation level through temperature measurement, a delicate balance can be struck to maintain the steam within the desired saturation level range at the sterilizer, with the steam generation system having been customized to each specific hospital by first being calibrated.

It is noted that, in an alternate embodiment, more than one sterilizer could be provided at different outlets of the steam generation system, with all sterilizers linked to a single or to multiple heat exchanger(s).

The invention claimed is:

1. A method of controlling the saturation level of a gaseous state first fluid generated at an outlet of a gaseous state fluid generation system, the gaseous state fluid generation system comprising a first fluid line circulating the first fluid therein, a second fluid line circulating a second fluid therein and a heat exchanger wherein the first fluid is heated by the second fluid so as to have the first fluid be in gaseous state at least at a first fluid outlet of the heat exchanger which is distinct and in fluid communication with the outlet of the gaseous state fluid generation system, said method comprising:
   a) generating gaseous state first fluid at the outlet of the gaseous state first fluid generation system and initially calibrating the gaseous state fluid generation system by:
      i) controlling a heat exchange value between the first and second fluids within the heat exchanger to obtain a set value for a reference parameter measured at a reference position on said first fluid line, with the reference parameter being representative of the saturation level of the first fluid;
      ii) taking a sample out of the gaseous state first fluid at the outlet of the gaseous state fluid generation system and determining a saturation level of the gaseous state first fluid at the outlet of the gaseous state fluid generation system from the sampled gaseous state first fluid;
      iii) if the saturation level of the gaseous state first fluid determined at step (ii) does not correspond to a first target saturation level of the gaseous state first fluid, controlling the heat exchange value of the heat exchanger to iteratively obtain different reference parameter values measured at the reference position and repeating step (ii) for each iteration of the reference parameter values until the first target saturation level of the gaseous state first fluid is determined at step (ii), with the first target saturation level of the gaseous state first fluid used to define an acceptable range of saturation levels; and
      iv) identifying the reference parameter value measured when the target saturation level is determined as the first target reference parameter value, with the first target reference parameter value used to define an acceptable range of reference parameter values;
and once the gaseous state fluid generation system is calibrated per step (a):
   b) measuring the reference parameter at the reference position while gaseous state first fluid is generated at the outlet of the gaseous state first fluid generation device;
   c) comparing the value of the reference parameter measured in step (b) to the acceptable range of target reference parameter values; and
   d) if the value of the reference parameter measured in step (b) falls outside of the acceptable range of reference parameter values, modifying the heat exchange value of the heat exchanger and repeating steps (b) and (c) until the value of the reference parameter measured in step (b) falls within the acceptable range of the reference parameter values, consequently controlling the saturation level of the gaseous state first fluid to have it fall within the acceptable range of saturation levels at the outlet of the gaseous state fluid generation system.

2. The method as defined in claim 1, wherein the reference parameter comprises a reference temperature, the reference position is located between the outlet of the heat exchanger and the outlet of the gaseous state fluid generation system, the target reference parameter value comprises a target temperature value and the first fluid is in superheated state at least at the reference position when the first fluid saturation level is at its first target saturation level at the outlet of the gaseous state fluid generation system.

3. The method as defined in claim 2, wherein the reference position is located near the outlet of the heat exchanger.

4. The method as defined in claim 2, wherein controlling and modifying the heat exchange value comprises controlling and modifying one of the second fluid debit through the heat exchanger, the temperature of the second fluid that flows through the heat exchanger, the second fluid pressure through the heat exchanger and a combination thereof.

5. The method as defined in claim 2, wherein the acceptable range of reference parameter values comprises reference temperature values equal to or above the target reference temperature value.

6. The method as defined in claim 2, wherein step (a)(iii) further comprises, if the saturation level of the first fluid determined at step (ii) does not correspond to a second target saturation level of the first fluid, the step of further controlling the heat exchange value of the heat exchanger to iteratively obtain different reference parameter values measured at the reference position and repeating step (ii) for each iteration of the reference parameter values until the second target saturation level of the first fluid is determined at step (ii), with the acceptable range of saturation levels of the first fluid being defined between the first and second target saturation levels of the first fluid; and wherein step (a)(iv) further comprises the step of identifying the reference parameter value measured when the second target saturation level is determined as a second target reference parameter value, with the acceptable range of reference parameter values being defined between the first and second target reference parameter values.

7. The method as defined in claim 6, wherein the gaseous state fluid generation system further comprises an electronic circuit capable of storing data therein, capable of processing data, and capable of data input and output, the step (a)(iv) comprises inputting and storing as data the acceptable range of reference parameter values in the electronic circuit, the step (b) comprises inputting as data the reference parameter value read in step (b), the step (c) comprises comparing through use of the electronic circuit the inputted reference parameter value read in step (b) to the stored acceptable range of reference parameter values and the step of modifying the heat exchange value of the heat exchanger in step (d) comprises automatically modifying through control by the electronic circuit the heat exchange value of the heat exchanger.

8. The method as defined in claim 2, wherein the gaseous state fluid generation system further comprises an electronic circuit capable of storing data therein, capable of processing data, and capable of data input and output, the step (a)(iv) comprises inputting and storing as data the acceptable range of reference parameter values in the electronic circuit, the step (b) comprises inputting as data the reference parameter value read in step (b), the step (c) comprises comparing through use of the electronic circuit the inputted reference parameter value read in step (b) to the stored acceptable range of reference parameter values and the step of modifying the heat exchange value of the heat exchanger in step (d) comprises automatically modifying through control by the electronic circuit the heat exchange value of the heat exchanger.

9. The method as defined in claim 2, wherein the step of calibrating the gaseous state first fluid generation system in step (a) comprises repeating steps (i) to (iv) at different first fluid line pressure values to obtain an acceptable range of reference parameter values for each first fluid line pressure value; and step (c) comprises comparing the reference parameter value measured in step (b) to the acceptable range of reference parameter values for a corresponding first fluid line pressure value that corresponds to an effective first fluid line pressure value.

10. The method as defined in claim 9, wherein the effective first fluid line pressure value is measured on the first fluid line when the reference parameter value is measured in step (b).

11. The method as defined in claim 2, wherein the reference parameter value measured in step (b) is compared in step (c) to a modified range of acceptable reference parameter values which is calculated based on the acceptable range of reference parameter values and on an effective first fluid line pressure value.

12. The method as defined in claim 11, wherein the effective first fluid line pressure value is measured on the first fluid line when the reference parameter value is measured in step (b).

13. The method as defined in claim 2, wherein the step (b) comprises one of continuously measuring the reference parameter value, discretely measuring the reference parameter value at regular or irregular time intervals and punctually measuring the reference parameter value.

14. The method as defined in claim 2, wherein the heat generation system further comprises a coalescing filter on the first fluid line upstream of said heat exchanger.

15. The method as defined in claim 2, wherein the first fluid is steam.

16. The method as defined in claim 15, wherein said gaseous state first fluid generation system further comprises a sterilizer connected to the outlet of the steam generation system for injecting steam generated by the gaseous state first fluid generation system in said sterilizer.

17. The method as defined in claim 1, wherein in step (a)(ii), determining the saturation level of the sampled gaseous state first fluid comprises measuring a sampled steam parameter other than the saturation level and correlating a saturation level with this sampled steam parameter.

18. The method as defined in claim 1, wherein the step of sampling the gaseous state first fluid and the step of determining the saturation level of the sampled gaseous state first fluid are accomplished by using a calorimeter.

* * * * *